US009715058B1

(12) United States Patent
Zhang et al.

(10) Patent No.: US 9,715,058 B1
(45) Date of Patent: Jul. 25, 2017

(54) ULTRAVIOLET LIGHT DEVICE (71) Applicant: Bolb Inc., San Jose, CA (US)

(72) Inventors: Jianping Zhang, Arcadia, CA (US); Ling Zhou, Dublin, CA (US); Ying Gao, Fremont, CA (US)

(73) Assignee: BOLB INC., San Jose, CA (US)

( * ) Notice: Subject to any disclaimer, the term of this patent is extended or adjusted under 35 U.S.C. 154(b) by 0 days.

(21) Appl. No.: 15/251,130

(22) Filed: Aug. 30, 2016

(51) Int. Cl.
*G02B 6/26* (2006.01)
*F21V 8/00* (2006.01)
*A61L 2/10* (2006.01)
*G02B 6/42* (2006.01)

(52) U.S. Cl.
CPC ............ *G02B 6/0061* (2013.01); *A61L 2/10* (2013.01); *G02B 6/009* (2013.01); *G02B 6/0031* (2013.01); *G02B 6/0043* (2013.01); *G02B 6/0045* (2013.01); *G02B 6/0053* (2013.01); *G02B 6/0055* (2013.01)

(58) Field of Classification Search
CPC .................................................. G02B 6/0043
See application file for complete search history.

(56) References Cited

U.S. PATENT DOCUMENTS

| 6,786,613 B2 | 9/2004 | Suzuki | |
| 6,814,456 B1 * | 11/2004 | Huang | ................. G02B 6/0051 362/218 |
| 7,160,003 B2 * | 1/2007 | Saitoh | .................. G02B 6/0038 362/330 |
| 7,648,250 B2 | 1/2010 | Lee | |
| 8,070,345 B2 * | 12/2011 | Zhang | .................. G02B 6/0043 362/619 |
| 8,226,286 B2 | 7/2012 | Lin et al. | |
| 8,353,617 B2 | 1/2013 | Montgomery et al. | |
| 8,403,511 B2 * | 3/2013 | Bae | ................... G02F 1/133603 362/330 |
| 8,849,079 B2 * | 9/2014 | Yoshida | ................... G02B 5/02 385/31 |
| 9,229,150 B2 | 1/2016 | Yang | |
| 2005/0276566 A1 * | 12/2005 | Iimura | ................. G02B 6/0018 385/146 |
| 2007/0171678 A1 * | 7/2007 | Shim | ..................... G02B 6/0016 362/616 |
| 2010/0149787 A1 * | 6/2010 | Zhang | .................. G02B 6/0043 362/97.1 |
| 2011/0051397 A1 * | 3/2011 | Bae | ................... G02F 1/133603 362/97.1 |

* cited by examiner

*Primary Examiner* — Rhonda Peace
(74) *Attorney, Agent, or Firm* — Patent Office of Dr. Chung Park (57) ABSTRACT

The invention relates to a light device that generates uniform light beam over a panel. A light device includes a light source and a light panel. The light panel includes: a lightguide that has an input port for receiving light from the light source, the input port is formed on a bottom surface of the lightguide; a beam reflector disposed on a top surface of the lightguide, the beam reflector reflects a portion of the light; a mirror disposed on the bottom surface of the lightguide, the mirror reflects a portion of the light toward the top surface; and a plurality of light scattering features disposed on the bottom surface of the lightguide, the plurality of light scattering features reflects a portion of the light toward the top surface.

15 Claims, 7 Drawing Sheets

ULTRAVIOLET LIGHT DEVICE

BACKGROUND

A. Technical Field

The present invention relates to lighting devices, and more particularly, to ultraviolet light panels for generating light with enhanced intensity uniformity.

B. Background of the Invention

Light (Display) panels are widely used in various devices, such as mobile phones, notebooks, desktop monitors, notepads, and so on. Typically, a display panel has a backlight source that provides light for the display panel. The state-of-the-art display panels adopt high-efficiency InGaN multiple-quantum-well (MQW) light-emitting diodes (LEDs) as backlight sources taking advantage of the up to 70% electricity-light conversion efficiency. The basic function of a light panel is to transform the LED's point light source into a uniform areal light source. As such, one of the challenges that a device designer encounters is to control the beam uniformity across the entire display panel. If the light intensity on a portion of the display panel is brighter and/or darker than the rest, not only the quality of the images displayed on the display panel is deteriorated, but also the lifetime of the device is shortened. Further, ultraviolet (UV) light panels can be realized by utilizing ultraviolet light sources as backlight. For example, AlGaN MQW LEDs emitting at wavelengths in the range of 240-365 nm can be used as ultraviolet light panel backlight sources for germicidal and medical applications. In this case, if the device is used to sterilize harmful germs/virus over a target area, a portion of the target area treated by the darker portion of the panel may not be sterilized to the intended level. Another challenge for a quality light panel is to reduce light loss during the light redistribution process. This is most critical for a UV light panel, since UV light loss is severer compared to visible light due to its shorter wavelength and higher photon energy resultant stronger scattering and absorption coefficient.

Figure 1A:
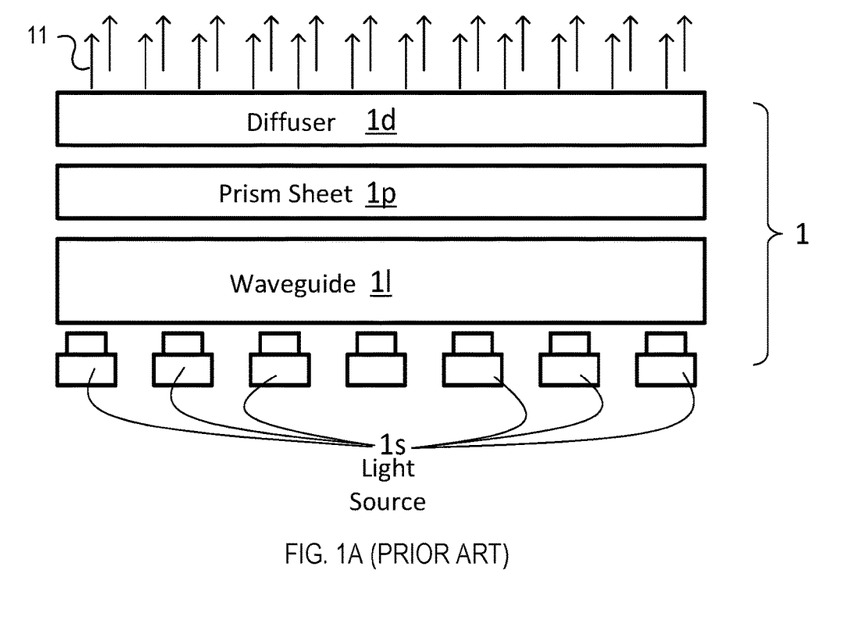
FIGS. 1A and 1B show schematic diagrams of conventional display panels.

FIG. 1A shows a schematic diagram of a conventional display panel 1. As depicted, the light sources, 1s, generate light that passes through the lightguide, 1l, prism sheet, 1p, and diffuser 1d, where the lightguide, prism sheet and diffuser convert the light beams from the discrete light sources 1s into the light 11 spread over the entire area of the panel. The display panel 1 has several drawbacks. First, since the light beams from the light sources 1s pass through multiple components, some portion of the light is absorbed by these components, reducing the overall efficiency of the panel. Second, the stacked components increase the form factor of the display panel 1, increasing the manufacturing cost of the panel and the form factor of the device that uses the panel.

Figure 1B:
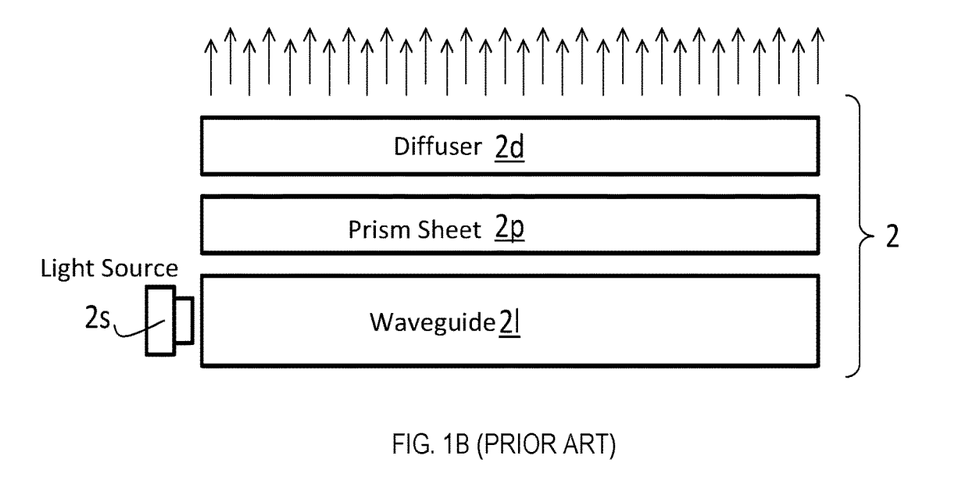

FIG. 1B shows another conventional display panel 2. As depicted, the light sources, 2s, generate light beams that pass through the lightguide, 2l, prism sheet, 2p, and diffuser 2d, where the lightguide, prism sheet and diffuser convert the light beams from the discrete light sources into the light spread over the entire area of the panel. Unlike the display panel 1, the lightguide 2l steers the direction of the light beams by about 90 degrees. As the light sources 2s are disposed on one side of the lightguide 21 to thereby reduce the overall thickness of the display panel 2, the reduction of thickness is obtained at the expense of area increase. Thus, the display panel 2 has the similar problems as the display panel 1.

Therefore, a better solution is needed to provide light panels with enhanced intensity uniformity and reduced form factors; moreover, a ultraviolet light panel is needed for transforming point or linear ultraviolet light source into uniform areal light source with minimal light loss.

SUMMARY OF THE DISCLOSURE

In one aspect of the present invention, a light panel includes: a light source, a lightguide having an input port for receiving light from the light source, the input port is formed on a bottom surface of the lightguide; a beam reflector disposed on a top surface of the lightguide facing against the input port, the beam reflector reflects a greater portion of the light and transmit a smaller portion of the light; a mirror disposed on the bottom surface of the lightguide, the mirror reflects a portion of the light toward the top surface; and a plurality of light scattering features disposed on the bottom surface of the lightguide, the plurality of light scattering features reflects a portion of the light toward the top surface, whereas the beam reflector steers the direction of most of the light beams from the input port by about 90 degrees, the mirror and the top surface of the lightguide provide guided modes for the steered light beams, and the scattering features extract portions of the steered light beams out of the lightguide into a direction substantially perpendicular to the lightguide top surface.

In another aspect of the present invention, a light device includes at least one light source and a light panel. The light panel includes i: a lightguide having at least one input port for receiving light from the at least one light source, the at least one input port is formed on a bottom surface of the lightguide; at least one beam reflector disposed on a top surface of the lightguide, the at least one beam reflector reflects a portion of the light; a mirror disposed on the bottom surface of the lightguide, the mirror reflects a portion of the light toward the top surface; and a plurality of light scattering features disposed on the bottom surface of the lightguide, the plurality of light scattering features reflects a portion of the light toward the top surface.

In still another aspect of the present invention, a light panel includes: a light source, a lightguide having an input port for receiving light from the light source, the input port is formed on a bottom surface of the lightguide; a beam reflector disposed on a top surface of the lightguide facing against the input port; a mirror disposed on the bottom surface of the lightguide; and a plurality of light scattering features disposed on the bottom surface of the lightguide, whereas the beam reflector steers the direction of most of the light beams from the input port by about 90 degrees, the mirror and the top surface of the lightguide provide guided modes for the steered light beams, and the scattering features steers portions of the steered light beams from the beam reflector by about another 90 degrees, such that light scattered by the scattering feature exits the light panel in the direction substantially parallel to the direction of the light beams received through the input port.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the invention. It will be apparent, however, to one skilled in the art that the invention can be practiced without these details. One skilled in the art will recognize that embodiments of the present invention, described below, may be performed in a variety of ways and using a variety of means. Those skilled in the art will also recognize additional modifications, applications, and embodiments are within the scope thereof, as are additional fields in which the invention may provide utility. Accordingly, the embodiments described below are illustrative of specific embodiments of the invention and are meant to avoid obscuring the invention.

A reference in the specification to "one embodiment" or "an embodiment" means that a particular feature, structure, characteristic, or function described in connection with the embodiment is included in at least one embodiment of the invention. The appearance of the phrase "in one embodiment," "in an embodiment," or the like in various places in the specification are not necessarily all referring to the same embodiment.

Figure 2:
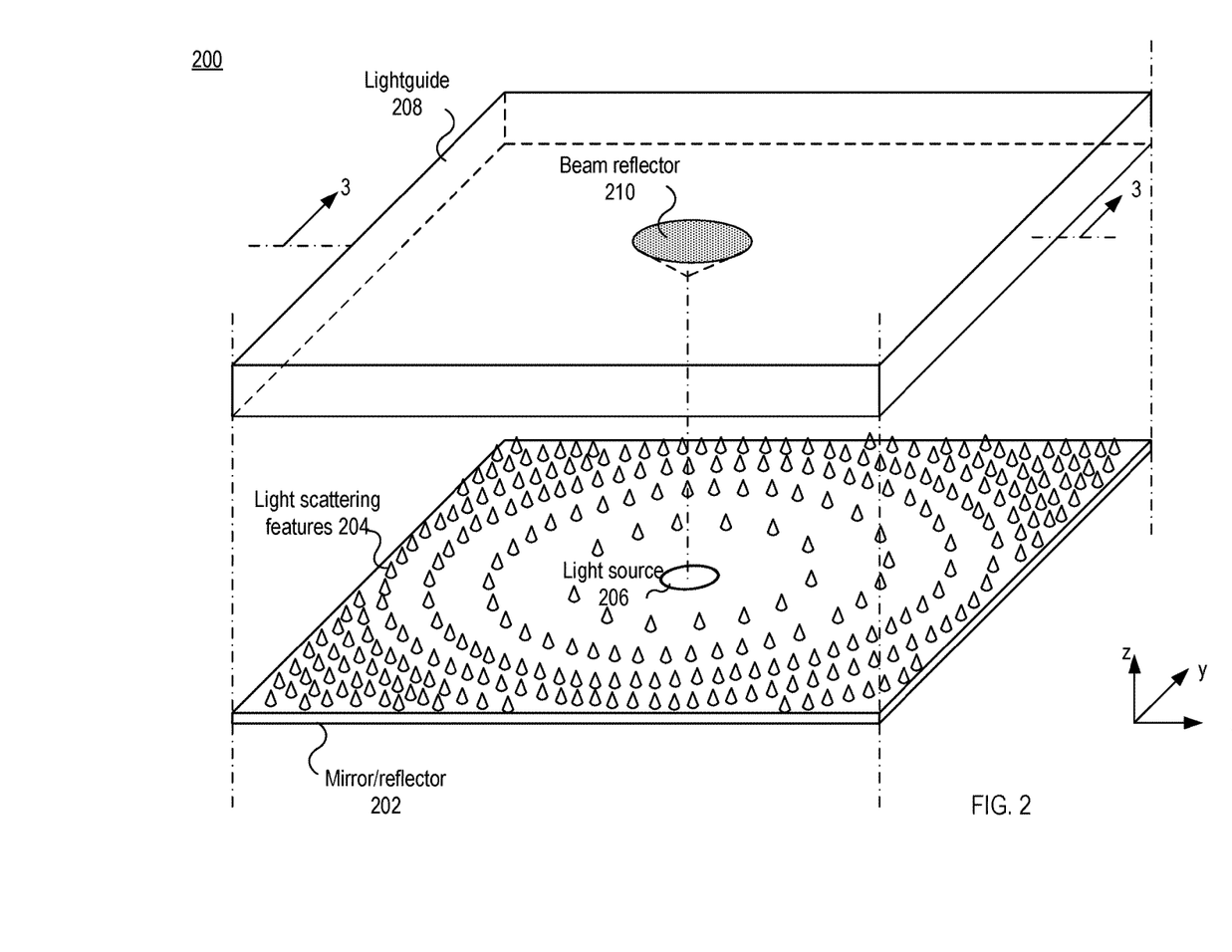
FIG. 2 shows an exploded perspective view of a light device according to embodiments of the present invention.
Figure 3:
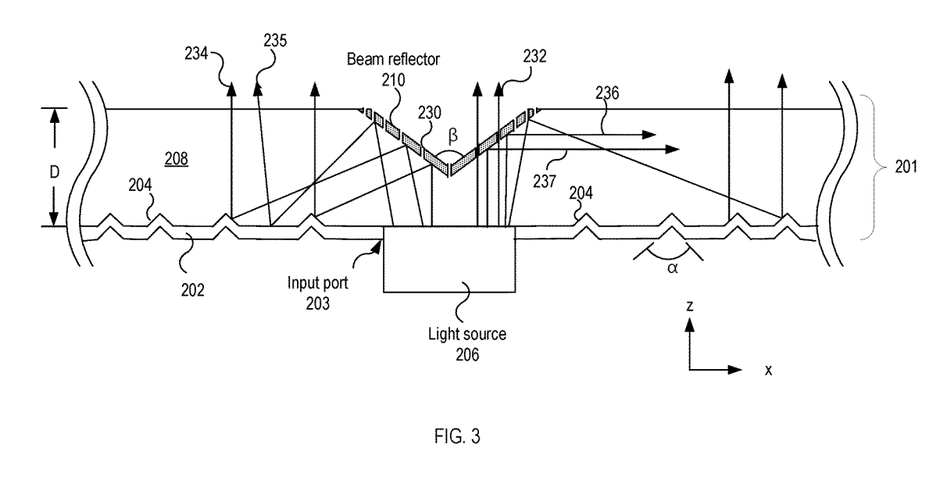
FIG. 3 shows a cross sectional view of the light device in FIG. 2, taken along the direction 3-3.

FIG. 2 shows an exploded perspective view of a light device 200 for generating light over a two dimensional area according to embodiments of the present invention. FIG. 3 shows a cross sectional view of the light device 200, taken along the direction 3-3 in FIG. 2. As depicted, the light device 200 may include: a light source 206 for generating light and a light panel 201 for converting the light from the light source into a uniform two dimensional light beam. The light panel 201 may include: a lightguide 208 through which the light travels; a beam reflector 210 disposed on the lightguide 208 and reflecting the light incident thereon; a mirror/reflector 202 disposed beneath the lightguide 208 and reflecting a portion of the light toward the top surface of the device 200; and a plurality of light scattering features 204 disposed beneath the lightguide 208 and reflecting a portion of the light toward the top surface of the device 200.

The light source 206 may be a point light source and generate light in a predetermined wavelength range. For instance, the light source may be a UV light source for sterilization, such as an AlGaN MQW LED emitting at wavelengths of 250, 265, 270, 280, 290, 310, or 340 nm, or a visible light emitting diode (LED) for displaying images on a display panel. It should be apparent to those of ordinary skill in the art that the light source 206 can be any other suitable type of light source that generates light having target intensity and wavelength.

For the purpose of illustration, only one light source 206 is shown in FIGS. 2 and 3. However, it should be apparent to those of ordinary skill in the art that more than one light source 206 can be installed beneath the lightguide 208.

In embodiments, the mirror/reflector 202 may be formed of light reflecting material, such as aluminum, silver or distributed Bragg reflector (DBR), and reflect light incident thereon. For instance, a light ray 235 reflected by the beam reflector 210 may be reflected by the mirror/reflector 202 and exit the lightguide 208. In embodiments, the mirror/reflector 202 may be deposited on the bottom surface of the lightguide 208 by a suitable deposition technique, such as chemical vapor deposition, or electron beam vapor deposition. The thickness of the mirror/reflector 202 may be determined by its material and the intended reflectance. For instance, reflecting material may be deposited on the bottom surface of the lightguide 208 at the thickness of 0.5-3.0 μm to have the reflectance of 90% or higher. It is noted that the mirror/reflector 202 may have any other suitable thickness as well as material.

The lightguide 208 may be formed of material that is transparent to the light generated by the light source 206. For instance, the lightguide 208 may be formed of quarts or sapphire if the light source 206 generates UV light. The lightguide 208 may include an input port 203 where the light source 206 is disposed so that the light enters the lightguide 208. If more than one light source is used (not shown in FIG. 2), the lightguide 208 may include more than one input port to accommodate the light sources. In embodiments, if the light source 206 is a line source, the lightguide 208 may have multiple input ports arranged along the longitudinal axis of light source 206 or have a shape of a slit. In embodiments, the thickness D of the lightguide 208 may range from 100 μm to 1 mm.

As discussed above, the mirror/reflector 202 may be formed by a conventional deposition technique. In such a case, a conventional lithography technique may be used to pattern the input port 203 so that the mirror/reflector 202 layer is not formed over the input port 203 during the deposition process. In embodiments, the light source 206 may be secured to the lightguide 208 or detachably coupled to the lightguide 208 or spaced-apart from the lightguide 208. In embodiments, the light source 206 may be formed on the bottom surface of the lightguide 208 by a suitable die attachment or deposition technique.

In embodiments, vertical light rays emitted by the light source 206 may be the reflected by the beam reflector 210 into transverse (nearly parallel to the surfaces of lightguide 208) light rays 236 and 237. Then, the transverse light ray 236 may be scattered into a different direction by a distant scattering feature 204 and exit the lightguide. Likewise, the transverse light ray 237 may be scattered by another distant scattering feature 204 and exit the lightguide 208. More specifically, a precisely horizontal ray may only hit the panel edge. However, substantially transverse rays may eventually hit the scattering features 204 and get steered an approximately 90 degree and exit upwardly.

The light scattering features 204 may be disposed on the bottom surface of the lightguide 208. In embodiments, the light scattering features 204 may be generated by etching the bottom surface of the lightguide 208 to form dimples/indentations and subsequently depositing light reflecting material on the dimples. In embodiments, the conventional lithography technique may be used to make a pattern for the light scattering features on the lightguide 208 and the conventional etching process may be used to make the dimples. In embodiments, the dimples may be formed on the lightguide 208 first and then, the mirror/reflector 202 may be formed by a thin film deposition process on the bottom surface of lightguide 208, whereas the light scattering features 204 may be simultaneously formed when the mirror material is conformally formed on the dimples/indentations. In embodiments, the dimples may be formed on the lightguide 208 via lapping or grinding.

In embodiments, if the lightguide 208 is fabricated by a molding process, the dimples may be formed on the bottom surface of the lightguide 208 during the molding process, i.e., the bottom surface of a mold may have a plurality of protrusions/bumps that correspond to the dimples. It is noted that other suitable techniques may be used to form the light scattering features 204 on the lightguide 208.

In embodiments, the light scattering features 204 may have a conical shape or a pyramid shape, even though any other suitable shape may be used to scatter the light incident thereon. In embodiments, as depicted in FIG. 3, the cross section of each light scattering feature 204 may have an isosceles triangle shape, where the vertex angle α may be in the range of 40-50 degrees, preferably about 45 degrees. In embodiments, the height of the light scattering features 204 along the z-axis may be in the rage of 0.2-3.0 µm. However, it is noted the height of the light scattering features 204 may vary depending on the size of the other components, such as the target light wavelength, the thickness of the lightguide 208 and the geometry of the beam reflector 210.

In embodiments, the light scattering feature 204 may be formed of light reflecting material, such as aluminum, silver or DBR, and reflect light incident thereon. For instance, a light ray 234 reflected by the beam reflector 210 may be reflected by the light scattering feature 204 and exit the lightguide 208. The thickness of the light scattering feature 204 may be determined by its material and the intended reflectance. For instance, reflecting material may be deposited on the dimples at the thickness of 0.5-3.0 µm to have the reflectance of 90% or higher. It is noted that the light scattering feature 204 may have any other suitable thickness as well as material.

As depicted in FIG. 2, the number density of the light scattering features 204 per unit area on the x-y plane may vary along the distance from the light source 206. In the lightguide 208, the light intensity per unit area may decrease as the distance from the light source 206 increases. Thus, to compensate the intensity variation, the number density of the light scattering features 204 may increase as the distance from the light source 206 increases, to thereby generate a uniform distribution of light over the entire area of the lightguide 208. In embodiments, the number density is highest at the peripheral edges of the lightguide 208 and lowest near the light source 206. In embodiments, the number density may be proportional to the distance from the light source 206. In embodiments, the number density may be exponentially proportional to the distance from the light source 206.

In embodiments, the beam reflector 210 may be formed on the top surface of lightguide 208, facing against light source 206. In embodiments, a conventional etching technique may be used to make a cavity in the top central portion of the lightguide 208. In embodiments, the cavity may be formed during the molding process of the lightguide 208. The cavity may have any suitable shape, such as a cone. Upon forming the cavity in the lightguide 208, a reflecting material may be deposited on the cavity using a conventional thin film deposition method, such as chemical vapor deposition technique, to form the beam reflector 210. In embodiments, the reflecting material may include aluminum, silver, DBR, or any other suitable material that can reflect light incident on thereon. In embodiments, the thickness of the beam reflector 210 may be 0.5-3.0 µm and have a reflectivity of 90% or higher.

The beam reflector 210 may convert the substantially vertical light rays (i.e., rays travelling in the z-axis direction) emitted by the light source 206 into transverse rays (i.e., substantially parallel to the surfaces of lightguide 208). A portion of the transverse rays, such as 235, may be reflected by the mirror/reflector 202 to exit the lightguide 208. Another portion of the transverse rays, such as 234, may be reflected by the light scattering features 204 to exit the lightguide 208. Yet another portion of the transverse rays, such as 236 and 237, may be scattered by distant light scattering features 204 to exit the lightguide, as discussed above. It is noted that according to this invention, the function of beam reflector 210 is to convert a majority of the vertically transmitted light rays from light source 206 into substantially horizontal transverse rays. The top and bottom surfaces of lightguide 208 thus provide waveguide effect for the transverse rays. The light scattering features 204 sitting on the bottom surface of lightguide 208 disrupt the waveguide process and scatter the transverse rays received by the scattering features 204 out of lightguide 208 in a direction substantially normal to its top surface. Even though not shown in FIGS. 2 and 3, in some other embodiments, light scattering features 204 may be formed on the top surface of lightguide 208.

In embodiments, the dimension, such as base diameter, of the beam reflector 210 along the x-axis may be equal to or larger than that of the light source 206 so that most of the light emitted by the light source 206 can be reflected by the beam reflector 210. The vertex angle β of the beam reflector 210 may be in the range of 80-100 degrees. The vertex angle β is used to control the reflected angle for the light beam vertically transmitted to the beam reflector 210. For a given size light source 206, the larger the horizontal lightguide dimension, the smaller the deviation of 13 to 90 degree.

In embodiments, the beam reflector 210 may include light transmission mechanism 230, such as via holes, that transmits light 232 therethrough. The diameter and number density of the holes 230 are determined such that the transmitted light intensity is substantially equal to the light intensity on the rest of the lightguide 208. In embodiments, the ratio between the total cross sectional area of the via holes 230 and the cross sectional area of the beam reflector 210 is substantially the same as the ratio between the cross sectional area of the light source 206 (or input port 203) and the cross sectional area of the lightguide 208. (Hereinafter, the term cross sectional area refers to the area projected onto the x-y plane.) For instance, the cross sectional area of the light source 206 may be 1 mm$^2$ and the cross sectional area of the lightguide 208 may be 4 cm$^2$. In such a case, the cross sectional area ratio between the light source 206 and the lightguide 208 is $2.5 \times 10^{-3}$. If the cross sectional area of the beam reflector is 1 mm$^2$, the total cross sectional area of the via holes 230 is $2.5 \times 10^{-3}$ mm$^2$ (=1 mm$^2 \times 2.5 \times 10^{-3}$).

In embodiments, the number density of via holes 230 may vary along the radial distance from the center of the beam reflector 210. This distribution is to provide a uniform output beam intensity over the beam reflector 210. For instance, the number density of the via holes 230 is lower at the center of the beam reflector 210 and higher near the circumferential edge of the beam reflector 210. In embodiments, the number density of the via holes 230 may be proportional to the radial distance from the center of the beam reflector 210. In embodiments, the via hoes 230 may be made by a conventional lithography and etching process, i.e., the beam reflector 210 may be patterned and etched to form the via holes 230. In embodiments, diameter of each via hole 230 may be in the order of submicrons or microns.

In embodiments, the light device 200 may include more than one light source. In such a case, the light device 200 may include more than one beam reflector that are disposed over the corresponding light sources to thereby reflect the light emitted by the light sources.

Figure 4:
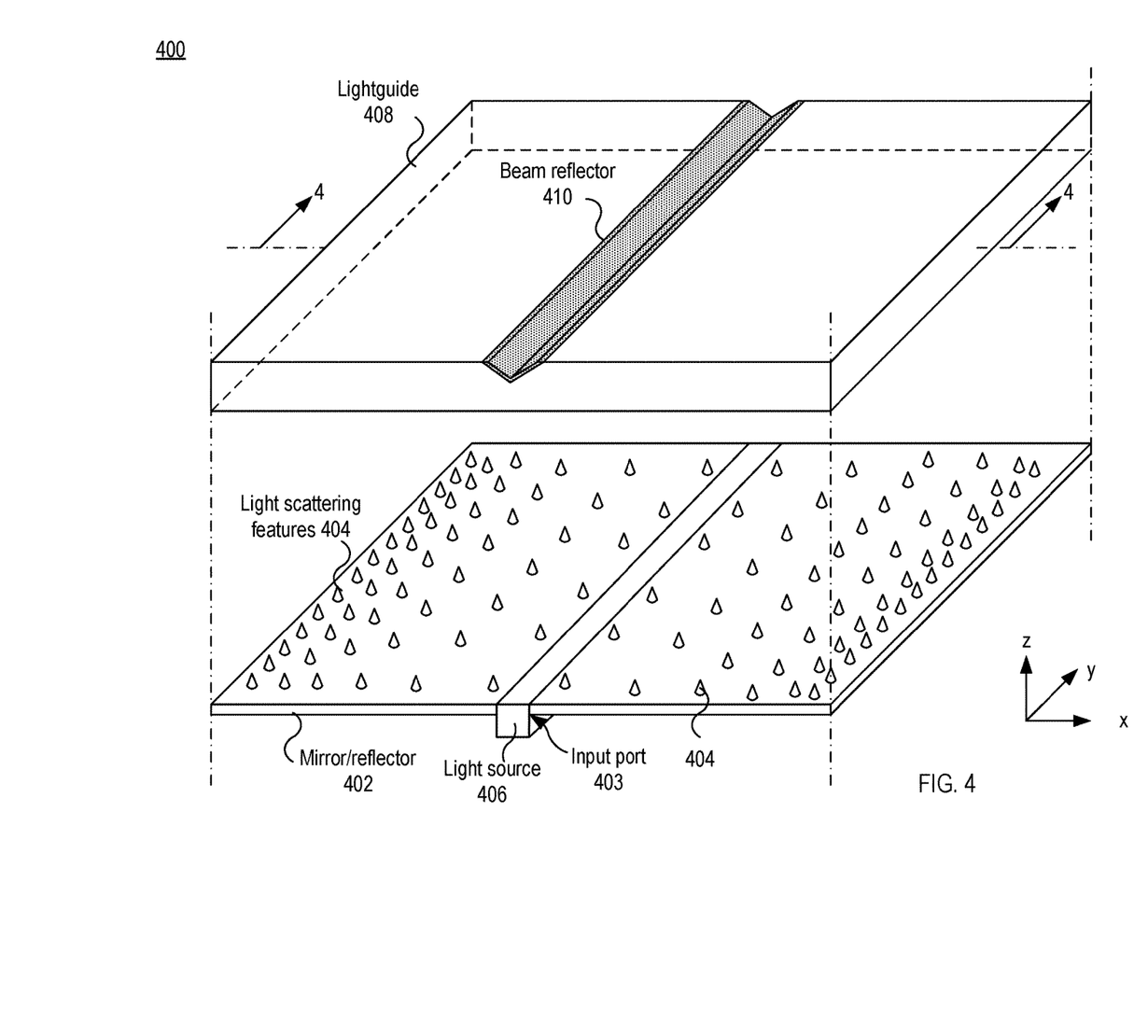
FIG. 4 shows a light device according to embodiments of the present invention.

FIG. 4 shows a light device 400 according to embodiments of the present invention. As depicted, the light device 400 may be similar to the light device 200, with the difference that the light source 406 is a linear light source that extends along the y-axis direction and the beam reflector 410 is a linear reflector that runs in parallel to the line source 406. The input port 403 may be configured to accommodate the linear light source 406 and extend along a longitudinal direction of the input port 403. In embodiments, the input port 403 may have a shape of a slit.

In embodiments, the beam reflector 410 may be a v-shaped channel and reflect the light emitted by the light source 406. In embodiments, the cross sectional shape of the beam reflector 410, taken along the direction 4-4, may be similar to the cross sectional shape of the beam reflector 210. In embodiments, the beam reflector 410 may be fabricated by the similar method as the beam reflector 210.

In embodiments, the beam reflector 410 may have multiple via holes, which are similar to the via holes 230 in terms of size, total cross sectional area and number density distribution. For instance, in embodiments, the number density of the via holes in the beam reflector 410 may vary along the distance in the x-axis direction. As the distance from the vertex of the beam reflector 410 increases, the number density of the via holes may increase. In embodiments, the number density may be proportional to the distance from the vertex of the beam reflector 410 along the x-axis.

In embodiments, the light scattering features 404 may be fabricated by the similar method as the beam reflector 204. Also, the light scattering features 404 may have the similar shape and be formed of similar material as the light scattering features 204. In embodiments, the number density of the light scattering features 404 may vary along the distance from the light source 406 (or input port 403) in the x-axis direction. In embodiments, as the distance from the light source 406 increases, the number density of the light scattering features 404 may increase. In embodiments, the number density may be proportional to the distance from the light source 406 along the x-axis.

The mirror/reflector 402, light scattering features 404, and lightguide 408 may have similar functions, be formed of similar materials and fabricated by the similar techniques as their counterparts in the light device 200.

Figure 5:
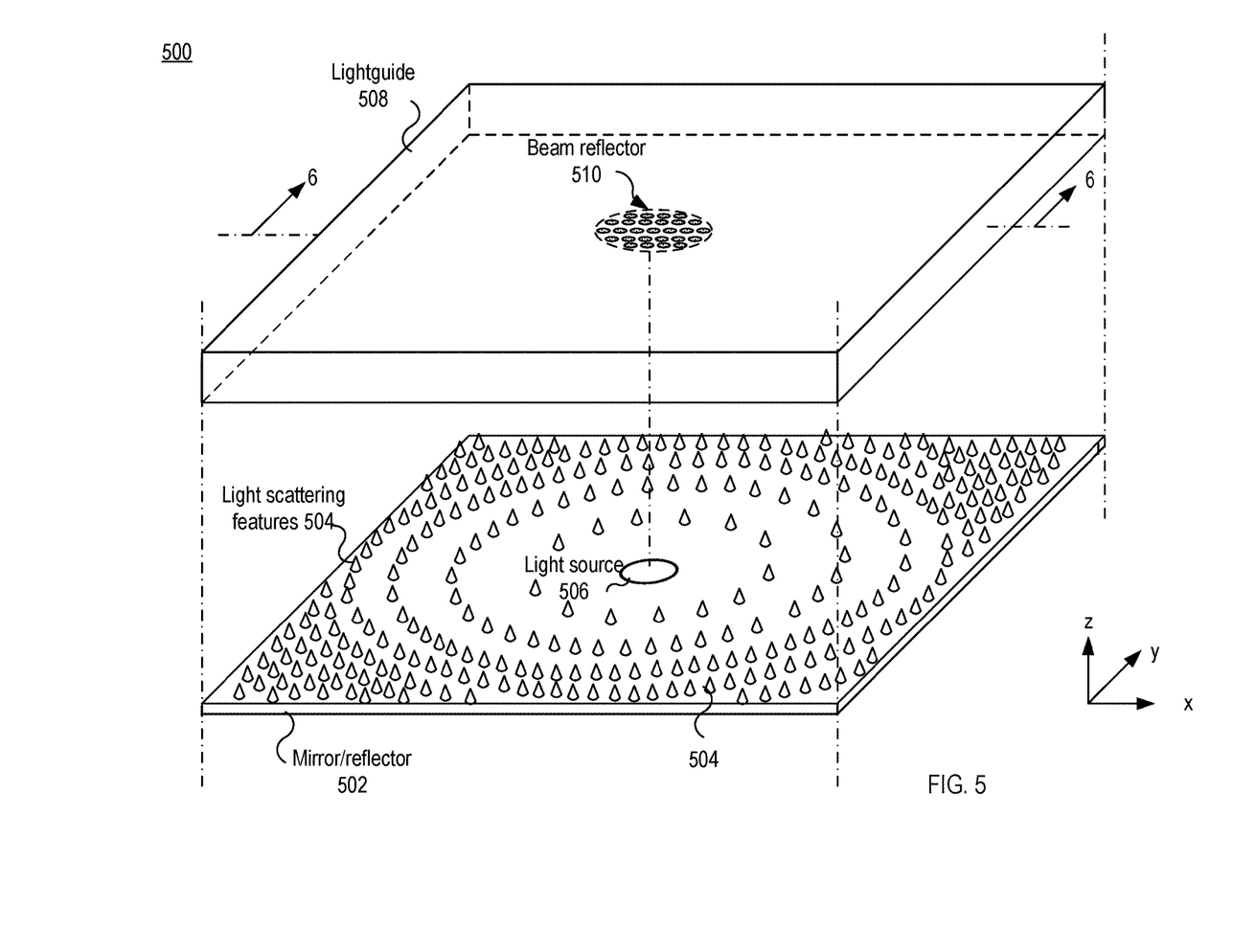
FIG. 5 shows a light device according to embodiments of the present invention.
Figure 6:
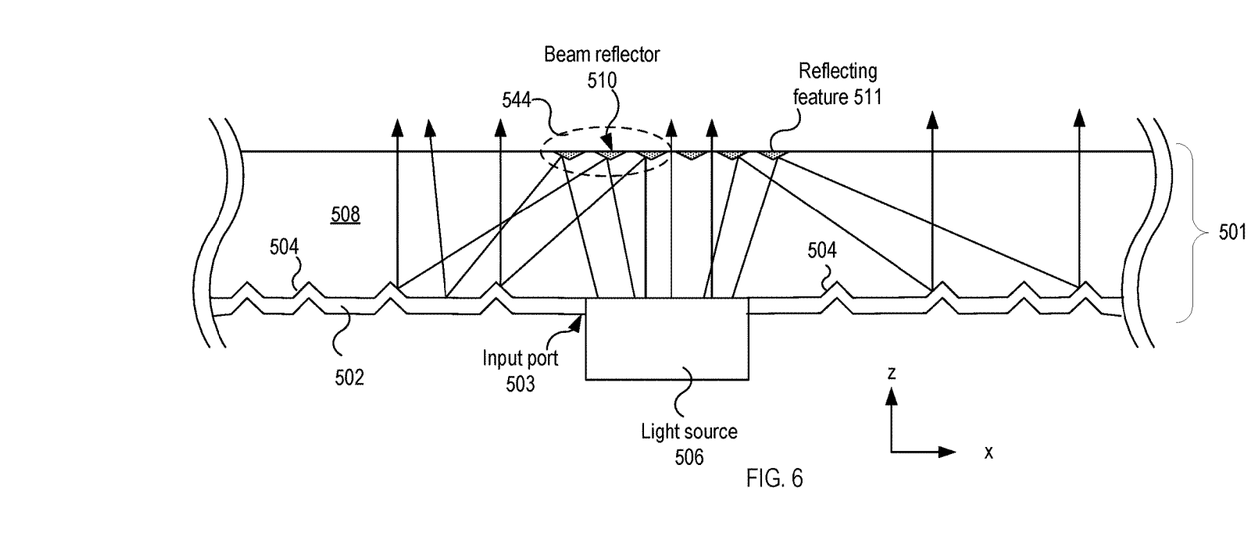
FIG. 6 shows a cross sectional view of the light device in FIG. 5, taken along the direction 6-6.
Figure 7:
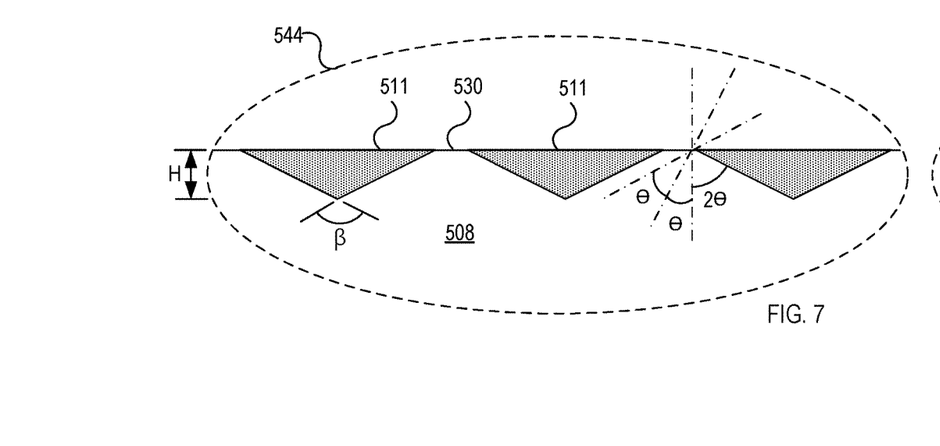
FIG. 7 shows an enlarged view of a portion of the light device in FIG. 6.

FIG. 5 shows a light device 500 according to embodiments of the present invention. FIG. 6 shows a cross sectional view of the light device in FIG. 5, taken along the direction 6-6. FIG. 7 shows an enlarged view of a portion 544 of the light device in FIG. 6. As depicted, the light device 500 may be similar to the light device 200, with the difference that the beam reflector 510 may have multiple reflecting features 511.

The reflecting features 511 may be disposed on the top surface of the lightguide 508. In embodiments, the reflecting features 511 may be generated by etching the top surface of the lightguide 508 to form dimples/indentations and subsequently depositing light reflecting material in the dimples. For instance, the conventional lithography techniques may be used to make a pattern for the reflecting features 511 on the lightguide 508 and the conventional etching process may be used to make the dimples. Then, the conventional thin film deposition technique may be used to fill reflecting material, such as aluminum, silver, and DBR, in the dimples. In embodiments, if the lightguide 508 is fabricated by a molding process, the dimples may be formed on the top surface of the lightguide 508 during the molding process, i.e., the top surface of a mold may have a plurality of protrusions/bumps that correspond to the dimples.

In embodiments, the reflecting features 511 may have a conical shape or a pyramid shape, even though any other suitable shape may be used to reflect the light emitted by the light source 506. In embodiments, the cross section of the each reflecting feature 511 may have an isosceles triangle shape with the vertex angle $\beta$. The vertex angle $\beta$ may be determined such that a light ray reflected by a reflecting feature 511 does not hit a neighboring reflecting feature 511. As depicted in FIG. 7, the angle $\theta$ between the x-axis and one side of the reflecting feature 511 satisfy the equation: $\theta + 2\theta = 90°$. Also, the vertex angle $\beta$ and the angle $\theta$ satisfy the equation: $\beta = 4\theta$. Thus, to prevent the reflected light ray from hitting the neighboring reflecting feature, the vertex angle $\beta$ may be greater than 120 degrees. In embodiments, the angle $\beta$ may be in the range of 0-180 degrees, preferably 120-130 degrees.

In embodiments, the vertical dimension H of the reflecting features 511 may be determined by its material and the intended reflectance. In embodiments, the vertical dimension H of the reflecting features 511 may be in the order of microns, for example, 0.5-2 microns. In embodiments, the reflecting features 511 may have the reflectance of 90% or higher. The beam reflector 510 may have the similar functions as the beam reflector 210, i.e., the beam reflector 510 may reflect the vertical light beam into the transverse light beam so that the light can exit the top surface of the lightguide 508 by the similar procedures as discussed in conjunction with the beam reflector 210.

In embodiments, the spaces 530 between reflecting features 511 may form a light transmission mechanism that transmits light therethrough. In embodiments, the spaces 530 may be arranged such that the intensity of the light transmitted through the spaces is substantially equal to the light intensity in the rest of the lightguide 508. In embodiments, the ratio between the total cross sectional area of the spaces 530 and the cross sectional area of the beam reflector 510 is the same as the ratio between the cross sectional area of the light source 506 and the cross sectional area of the lightguide 508. For instance, the cross sectional area of the light source 506 may be 1 $mm^2$ and the cross sectional area of the lightguide 508 on the x-y plane may be 4 $cm^2$. In such a case, the cross sectional area ratio between the light source 506 and the lightguide 508 is $2.5 \times 10^{-3}$. If the cross sectional area of the beam reflector 510 is 1 $mm^2$, the total cross sectional area of the spaces 530 is $2.5 \times 10^{-3}$ $mm^2$ (=1 $mm^2 \times 2.5 \times 10^{-3}$). In embodiments, spacing between neighboring reflecting features 511 may be in the order of submicrons or microns.

In embodiments, the size of the spaces 530 may vary along the radial distance from the center of the beam reflector 510. This variation is to provide a uniform output beam intensity over the beam reflector 510. For instance, the spacing is larger near the center of the beam reflector 510 and smaller near the circumferential edge of the beam reflector 510. In embodiments, the spacing may be proportional to the radial distance from the center of the beam reflector 510.

In embodiments, the components of the light panel 501, i.e., lightguide 508, light scattering features 504, input port 503, and mirror/reflector 502, may have the similar functions, be formed of similar materials and fabricated by the similar techniques as their counterparts of the light panel 201. It is noted that the light device 500 may have more than one light source and more than one beam reflector. It is also noted that, in embodiments, the light source 506 may be a linear light source that is similar to the light source 406. In such a case, the projected area of the beam reflector 910 may have a rectangular shape the beam reflector 510 may have a substantially rectangular shape and be disposed over the light source to thereby cover the entire portion of the linear light source.

Figure 8:
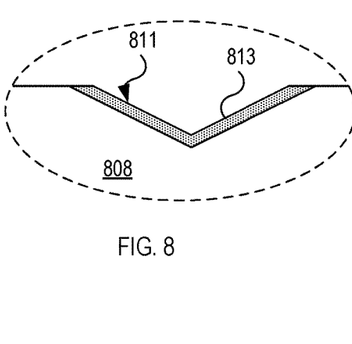
FIG. 8 shows a cross sectional view of a reflecting feature according to embodiments of the present invention.

FIG. 8 shows a cross sectional view of a reflecting feature 811 according to embodiments of the present invention, where the reflecting feature 811 may be used in place of the reflecting feature 511. As depicted, the reflecting feature 811 is similar to the reflecting feature 511, with the difference that a reflecting layer 813 is formed on the bottom side. The reflecting feature 811 may be fabricated by the conventional lithography and etching techniques to make the dimples and by the conventional deposition technique to deposit the reflecting layer 813 on the dimples.

Figure 9:
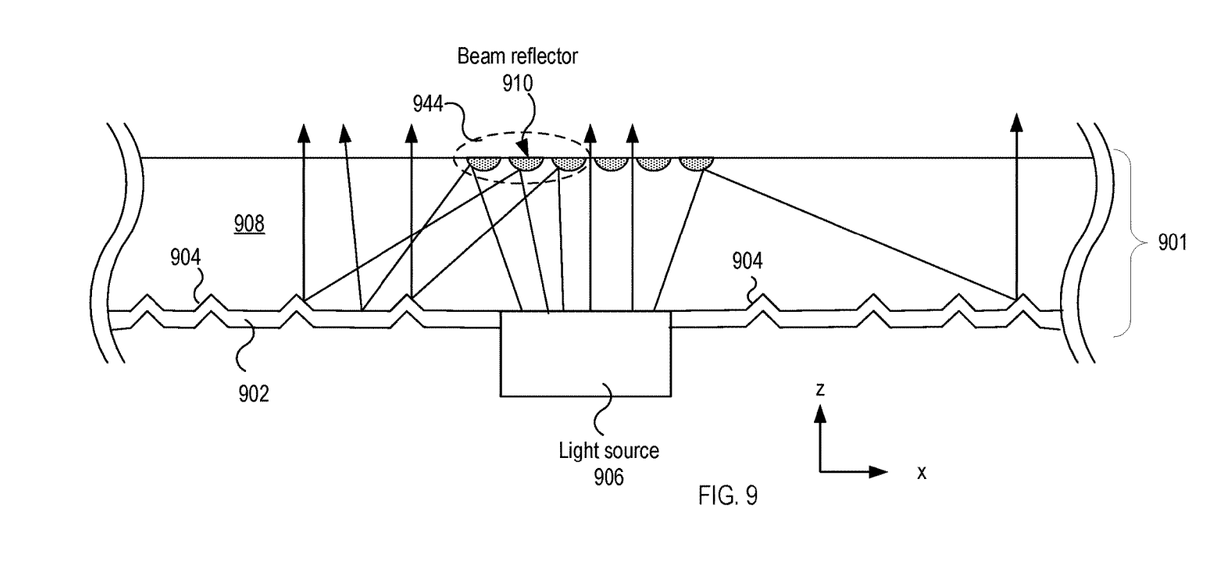
FIG. 9 shows a cross sectional view of a light device according to embodiments of the present invention.
Figure 10:
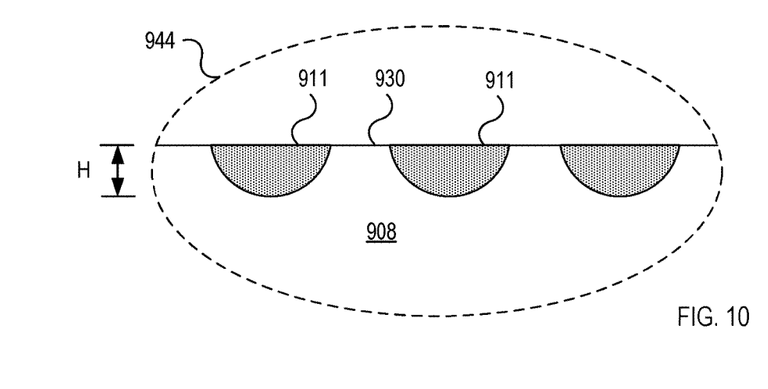
FIG. 10 shows an enlarged view of a portion of the light device in FIG. 9.

FIG. 9 shows a cross sectional view of a light device 900 according to embodiments of the present invention. FIG. 10 shows an enlarged view of a portion 944 of the light device in FIG. 9. As depicted, the light device 900 is similar to the light device 500, with the difference that the reflecting features 911 has a shape of a portion of a sphere, such as hemisphere.

In embodiments, the vertical dimension H of the reflecting features 911 may be in the order of microns. The material and fabrication method of the reflecting features 911 may be similar to those of the reflecting features 511. For instance, the lightguide 908 may be etched to form dimples first and filled with the reflecting material by the conventional chemical vapor deposition technique. In another example, the dimples are made during the molding process of the lightguide 908.

In embodiments, the components of the light panel 901, i.e., lightguide 908, light scattering features 904, and mirror/reflector 902, may have the similar functions, be formed of similar materials and fabricated by the similar techniques as their counterparts of the light panel 501. It is noted that the light device 900 may have more than one light source and more than one beam reflector. It is also noted that, in embodiments, the light source 906 may be a linear light source that is similar to the light source 406. In such a case, the projected area of the beam reflector 910 may have a rectangular shape and be disposed over the light source to thereby cover the entire portion of the linear light source.

In embodiments, the size of the spaces 930 between neighboring reflecting features 911 may be determined using the same principles as discussed above in conjunction with the spaces 530. For instance, the size of the spaces 930 may vary along the radial distance from the center of the beam reflector 910.

Figure 11:
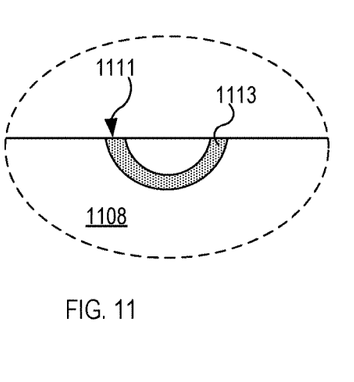
FIG. 11 shows a cross sectional view of a reflecting feature according to embodiments of the present invention.

FIG. 11 shows a cross sectional view of a reflecting feature 1111 according to embodiments of the present invention, where the reflecting feature 1111 may be used in place of the reflecting feature 911. As depicted, the reflecting feature 1111 is similar to the reflecting feature 911, with the difference that a reflecting layer 1113 is formed on the bottom side. The reflecting feature 1111 may be fabricated by the conventional lithography, etching technique and deposition technique. For instance, the lightguide 1108 may be patterned and etched to form dimples and then, the reflecting material is deposited on the dimples by the chemical vapor deposition technique.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A light panel, comprising:
    a lightguide having an input port for receiving light, the input port is disposed on a bottom surface of the lightguide;
    a beam reflector disposed on a top surface of the lightguide, the beam reflector reflects at least a portion of the light;
    a mirror disposed on the bottom surface of the lightguide, the mirror reflects a portion of the light toward the top surface of the lightguide; and
    a plurality of light scattering features disposed on the bottom surface of the lightguide, the plurality of light scattering features reflects a portion of the light toward the top surface of the lightguide,
    wherein a portion of the lightguide is removed to form a cavity in the lightguide and the beam reflector includes a light reflecting layer deposited on the cavity, the beam reflector includes a plurality of via holes for transmitting a portion of the light therethrough and a number density of the plurality of via holes is proportional to a distance from a center of the beam reflector.

2. A light panel as recited in claim 1, wherein a number density of the plurality of light scattering features is proportional to a distance from the input port.

3. A light panel as recited in claim 1, wherein a ratio between a total cross sectional area of the plurality of via holes and a cross sectional area of the beam reflector is same as a ratio between a cross sectional area of the input port and a cross sectional area of the lightguide.

4. A light panel as recited in claim 1, wherein the beam reflector includes a plurality of reflecting features that are spaced apart from each other.

5. A light panel as recited in claim 4, wherein a size of a space between two neighboring ones of the plurality of reflecting features is proportional to a distance from a center of the beam reflector.

6. A light panel as recited in claim 4, wherein a ratio between a total cross sectional area of spaces between the plurality of reflecting features and a cross sectional area of the beam reflector is same as a ratio between a cross sectional area of the input port and a cross sectional area of the lightguide.

7. A light panel as recited in claim 4, wherein the plurality of reflecting features include a plurality of dimples formed on the top surface of the lightguide and a light reflecting material that at least partially fills in the plurality of dimples.

8. A light panel as recited in claim 7, wherein a cross section of each said dimple has a shape of at least one selected from the group consisting of an isosceles triangle and a portion of a circle.

9. A light panel as recited in claim 4, wherein the input port is configured to accommodate a linear light source and the plurality of reflecting features are disposed along a longitudinal direction of the input port.

10. A light panel as recited in claim 1, wherein the input port is configured to accommodate a linear light source and the beam reflector extends along a longitudinal direction of the input port.

11. A light panel as recited in claim 1, wherein the input port is configured to accommodate a linear light source and the cavity is a v-shaped channel that extends along a longitudinal direction of the input port.

12. A light device, comprising:
at least one light source;
and a light panel, including;
  a lightguide having at least one input port for receiving light from the at least one light source, the at least one input port is formed on a bottom surface of the lightguide;
  at least one beam reflector disposed on a top surface of the lightguide, the at least one beam reflector reflects at least a portion of the light;
  a mirror disposed on the bottom surface of the lightguide, the mirror reflects a portion of the light toward the top surface of the lightguide; and
  a plurality of light scattering features disposed on the bottom surface of the lightguide, the plurality of light scattering features reflects a portion of the light toward the top surface of the lightguide,
  wherein a portion of the lightguide is removed to form at least one cavity in the lightguide and the at least one beam reflector includes a light reflecting layer deposited on the at least one cavity, the at least one beam reflector includes a plurality of via holes for transmitting a portion of the light therethrough and a number density of the plurality of via holes is proportional to a distance from a center of the at least one beam reflector.

13. A light device as recited in claim 12, wherein the at least one light source includes at least one selected from the group consisting of a point light source and a linear light source.

14. A light device as recited in claim 12, where the at least one light source includes a UV light source.

15. A light panel, comprising:
a lightguide having an input port for receiving light, the input port is disposed on a bottom surface of the lightguide;
a beam reflector disposed on a top surface of the lightguide, the beam reflector reflects at least a portion of the light;
a mirror disposed on the bottom surface of the lightguide, the mirror reflects a portion of the light toward the top surface of the lightguide; and
a plurality of light scattering features disposed on the bottom surface of the lightguide, the plurality of light scattering features reflects a portion of the light toward the top surface of the lightguide,
wherein the beam reflector includes a plurality of reflecting features that are spaced apart from each other and wherein a ratio between a total cross sectional area of spaces between the plurality of reflecting features and a cross sectional area of the beam reflector is same as a ratio between a cross sectional area of the input port and a cross sectional area of the lightguide.

* * * * *